United States Patent [19]

Rieke

[11] Patent Number: 5,231,205
[45] Date of Patent: Jul. 27, 1993

[54] PREPARATION AND USE OF (2-BUTENE-1,4-DIYL)MAGNESIUM COMPLEXES IN ORGANIC SYNTHESIS

[75] Inventor: Reuben D. Rieke, Lincoln, Nebr.

[73] Assignee: Board of Regents of the University of Nebraska, Lincoln, Nebr.

[21] Appl. No.: 763,629

[22] Filed: Sep. 23, 1991

[51] Int. Cl.$^5$ .............................................. C07F 7/08
[52] U.S. Cl. .................... 556/406; 556/449; 556/466; 260/665 R; 560/129; 568/817; 568/819; 568/870; 568/393; 568/374; 558/365; 558/366; 558/384; 570/186; 585/360; 585/361
[58] Field of Search .................... 260/665 R; 556/449, 556/465, 406; 560/129; 568/817, 819, 820, 343, 374; 558/365, 366, 384; 570/186, 187; 585/360, 361

[56] References Cited

U.S. PATENT DOCUMENTS

| | | | |
|---|---|---|---|
| 4,087,468 | 5/1978 | Solomon | 568/807 |
| 4,166,898 | 9/1979 | Kambe | 528/405 |
| 4,731,203 | 3/1988 | Bogdanovic | 260/665 G |

OTHER PUBLICATIONS

S. Akutagawa et al., *J. Am. Chem. Soc.*, 98, 7420 (1976).
R. Baker et al., *J.C.S. Perkin I*, 1815 (1976).
B. Bogdanovic, *Acc. Chem. Res.*, 21, 261 (1988).
T. P. Burns et al., *J. Org. Chem.*, 48, 4141 (1983).
T. P. Burns et al., *J. Org. Chem.*, 52, 3674 (1987).
U. M. Dzemilev et al., *J. Organomet. Chem.*, 406, 1 (1991).
E. Erdik, *Tetrahedron*, 40, 641 (1984).
G. Erker et al., *Adv. Organomet. Chem.*, 24, 1 (1985).
P. K. Freeman et al., *J. Org. Chem.*, 48, 879 (1983).
K. Fujita et al., *J. Organomet. Chem.*, 113, 201 (1976).
S. Harvey et al., *J. Org. Chem.*, 53, 3134 (1988).
Y. Kai et al., *Chem. Lett.*, 1277 (1982).
D. W. Knight, *Gen. Synth. Methods*, 6, 277 (1983).
W. E. Lindsell, *Comprehensive Organometallic Chemistry*, Ch. 4.1 and 4.2, Wilkinson, ed., Pergamon Press, Oxford (1982).
R. M. Magid, *Tetrahedron*, 36, 1901 (1980).
Y. Nakano et al., *Tetrahedron Lett.*, 28, 2833 (1972).
E. Negishi, *Pure & Appl. Chem.*, 53, 2333 (1981).
W. J. Richter, *J. Organomet. Chem.*, 289, 45 (1985).
R. D. Rieke et al., *J. Amer. Chem. Soc.*, 94, 7178 (1972).
R. D. Rieke et al., *J.C.S. Chem. Comm.*, 879 (1973).
R. D. Rieke et al., *J. Amer. Chem. Soc.*, 96, 1775 (1974).
R. D. Rieke, *Acc. Chem. Res.*, 10, 301 (1977).
R. D. Rieke, "Use of Activated Metals in Organic and Organometallic Synthesis", *Top. Curr. Chem.*, 59, 1 (1975).
R. D. Rieke, *U.S. NTIS, AD Rep.*, Number: AD-A150026, pp. 1-18 (Citation: Gov. Rep. Announce, Index (U.S.) 1978, 78(1), 171).

(List continued on next page.)

*Primary Examiner*—Paul F. Shaver
*Attorney, Agent, or Firm*—Merchant, Gould, Smith, Edell, Welter & Schmidt

[57] ABSTRACT

The magnesium complexes of cyclic hydrocarbons, such as 1,2-dimethylenecycloalkanes, are readily prepared in high yields using highly reactive magnesium. Reactions of these (2-butene-1,4-diyl)magnesium reagents with electrophiles such as dibromoalkanes, alkylditosylates, or bromoalkylnitriles serve as a convenient method for synthesizing spirocyclic systems. Significantly, spirocarbocycles prepared by this method contain functional groups such as the exocyclic double bond or a keto group in one of the rings which could be used for further elaboration of these molecules. Furthermore, fused bicyclic systems containing a substituted five-membered ring can be conveniently prepared at high temperatures by the reactions of (2-butene-1,4-diyl)magnesium complexes with carboxylic esters and acids whereas low temperatures lead to regioselective synthesis of $\beta,\gamma$-unsaturated ketones.

20 Claims, No Drawings

OTHER PUBLICATIONS

R. D. Rieke, *Report* (1985) Number: DOE/ER/106-03-T3; Order No. DE85014844, 18 pp. (Citation: Energy Res. Abstr. (1985) 10(18), Abstr. No. 37255).

R. D. Rieke et al., *J. Org. Chem.*, 46, 4323 (1981).

R. D. Rieke et al., *High Energy Processes in Organometallic Chemistry*, K. S. Suslick, Ed., (ACS Symposium Series 333: American Chemical Society: Washington D.C., 1987) pp. 223–245.

R. D. Rieke, *Science*, 246, 1260 (1989).

R. D. Rieke et al., *Tetrahedron*, 45, 443 (1989).

R. D. Rieke et al., *J. Org. Chem.*, 56, 3109 (1991).

R. G. Salomon, *J. Org. Chem.*, 39, 3602 (1974).

M. Vandewalle et al., *Tetrahedron*, 41, 1767 (1985).

D. Walther et al., *Naturwiss. Reihe.*, 34, 789 (1985) (*Chem Abs.*, 105, 746 (1986), Abstract No. 105:42862z).

P. A. Wender et al., *J. Am. Chem. Soc.*, 110, 2218 (1988).

T.-C. Wu et al., *J. Org. Chem.*, 55, 5045 (1990).

H. Xiong et al., *J. Org. Chem*, 54, 3247 (1989).

H. Xiong et al., *Tetrahedron Lett.*, 32, 5269 (1991).

M. Yang et al., *Tetrahedron Letters*, 44, 3843 (1970).

H. Yasuda et al., *Acc. Chem. Res.*, 18, 120 (1985).

H. Yasuda et al., *Recent Advances in Anionic Polymerization*, Hogen-Esch, T. E. and Smid, J., Ed.; 1987, pp. 59–71.

PREPARATION AND USE OF (2-BUTENE-1,4-DIYL)MAGNESIUM COMPLEXES IN ORGANIC SYNTHESIS

The present invention was made with Government support under Contract No. GM35153 awarded by the National Institute of Health. The Government has certain rights in the invention.

BACKGROUND OF THE INVENTION

Metallic magnesium is known to react with certain 1,3-dienes yielding halide-free organomagnesium compounds. These reactions are typically catalyzed by alkyl halides or transition metal salts. The dienemagnesium compounds produced from these reactions have been mainly limited to open-chain 1,3-dienes, including 1,3-butadiene, 2-methyl-1,3-butadiene, i.e., isoprene, 1-methyl-3-methylene-1,6-octadiene, i.e., myrcene, 2,3-dimethyl-1,3-butadiene, and (E,E)-1,4-diphenyl-1,3-butadiene.

There are problems associated with the preparation of these reagents using metallic magnesium, however. For example, the reaction of metallic magnesium with 1,3-dienes such as 1,3-butadiene or isoprene usually involves dimerization, trimerization, or oligomerization of the product. Furthermore, the reactions are generally accompanied by a variety of by-products. Consequently, the utilization of these reagents in organic synthesis has been quite limited, except for perhaps the use of 1,3-butadienemagnesium in organometallic synthesis.

It has recently been demonstrated that substituted (2-butene-1,4-diyl)magnesium complexes can be prepared using highly reactive magnesium, produced from $MgCl_2$, Li, and naphthalene in tetrahydrofuran, and 1,4-diphenyl-1,3-butadiene or 2,3-dimethyl-1,3-butadiene. These halide-free organomagnesium reagents contain two formal Mg-C bonds in one organic species and have been shown to function as bisnucleophiles in reactions with electrophiles. For example, these bis-Grignard reagents formed from 1,3-butadienes react with $\alpha,\omega$-alkylene dihalides in either 1,2-, 1,4-, or 2,1- additions to give complex carbocycles.

Although reactions of highly reactive magnesium with symmetrical 1,3-dienes, specifically, 1,4-diphenyl-1,3-butadiene and 2,3-dimethyl-1,3-butadiene, have been shown, reactions with more complex 1,3-dienes have not been discussed to any significant extent in the literature. Thus, it is an object of this invention to prepare (2-butene-1,4-diyl)magnesium complexes from more complex 1,3-diene systems than simple symmetrical 1,3-butadienes such as 1,4-diphenyl-1,3-butadiene and 2,3-dimethyl-1,3-butadiene. Furthermore, it is an object of this invention to utilize such (2-butene-1,4-diyl)magnesium complexes in organic synthesis.

SUMMARY OF THE INVENTION

The present invention is directed to a method for the preparation of spirocycles. The method consists of: contacting a magnesium(II) salt in an ethereal, polyethereal, or hydrocarbon solvent, preferably an ethereal or polyethereal solvent, and more preferably tetrahydrofuran, with a reducing agent having a reduction potential of about $-1.5$ volts, or more negative, to form a highly reactive magnesium species; and contacting the highly reactive magnesium species with a cyclic hydrocarbon containing at least two conjugated exocyclic double bonds to form a (2-butene-1,4-diyl)magnesium complex. Preferably, the method further includes a step of contacting the (2-butene-1,4-diyl)magnesium complex with an electrophile to form a spirocycle.

The cyclic hydrocarbon is preferably a cycloalkane containing two conjugated exocyclic double bonds. More preferably, the cyclic hydrocarbon is selected from the group consisting of 1,2-dimethylenecyclohexane, 1,2-dimethylenecyclopentane, and 1,2-dimethylenecycloheptane. The step of contacting the highly reactive magnesium species with a cyclic hydrocarbon is preferably carried out in an ethereal or polyethereal solvent.

The electrophiles used in the reaction with the (2-butene-1,4-diyl)magnesium complexes to form the spirocycles are preferably selected from the group consisting of organodihalides, organoditosylates, haloalkylnitriles, esters, and acids. More preferably, the electrophiles are selected from the group consisting of alkyldibromides, alkylditosylates, and bromoalkylnitriles. The step of contacting the (2-butene-1,4-diyl)magnesium complex with an electrophile is carried out at a temperature below about 100° C., and in an ethereal or polyethereal solvent.

The reducing agent used in the step of forming the highly reactive magnesium species is preferably an alkali metal salt of an aromatic anion. More preferably, the reducing agent is selected from the group consisting of sodium or lithium naphthalenide, anthracenide, or biphenylide. Most preferably, the reducing agent is preformed lithium naphthalenide.

The present invention is also directed to a method for the preparation of a fused ring carbocyclic alcohol. The method includes the steps of: contacting a magnesium(II) salt in an ethereal, polyethereal, or hydrocarbon solvent with a reducing agent having a reduction potential of about $-1.5$ volts, or more negative, to form a highly reactive magnesium species; contacting the highly reactive magnesium species with a cyclic hydrocarbon containing at least two conjugated exocyclic double bonds to form a (2-butene-1,4-diyl)magnesium complex; and contacting the (2-butene-1,4-diyl)magnesium complex with a carboxylic ester or acid in an ethereal or polyethereal solvent at a temperature of about 25° C. or greater to form a fused ring carbocyclic alcohol. By changing the reaction temperature of the latter step of this reaction, $\beta,\gamma$-unsaturated ketones can be prepared. That is, by contacting the (2-butene-1,4-diyl)magnesium complex with a carboxylic ester or acid in an ethereal or polyethereal solvent at a temperature of below about $-10°$ C., a $\beta,\gamma$-unsaturated ketone is formed.

DETAILED DESCRIPTION

The present invention is directed to the discovery that novel (2-butene-1,4-diyl)magnesium complexes can be prepared using a highly reactive magnesium metal species and symmetrical or unsymmetrical 1,3-dienes including cyclic hydrocarbons containing at least two conjugated exocyclic double bonds. Specifically, the invention involves a method for the one-step formation of spirocycles, fused ring carbocyclic alcohols, and $\beta,\gamma$-unsaturated ketones using suitable electrophiles and (2-butene-1,4-diyl)magnesium complexes prepared from cyclic hydrocarbons containing at least two conjugated exocyclic double bonds. Also, silicon-containing spiroheterocycles can be prepared from unsymmetrical (2-butene-1,4-diyl)magnesium complexes using silicon halides. The invention also involves a method for the control of the regioselectivity of electrophilic attack of unsymmetrical (2-butene-1,4-diyl)magnesium complexes using triorganosilyl chlorides prior to reaction with a second electrophile.

The Magnesium Species

The highly reactive magnesium species is composed of formally zerovalent magnesium metal atoms in the form of a finely divided black powder. By "formally zerovalent" it is meant that the formal oxidation state, or charge, is equal to the group number (i.e., 2) minus the number of unshared electrons (i.e., 2) minus the number of bonds (i.e., 0).

The highly reactive magnesium species of the present invention is prepared from the reduction of a magnesium(II) salt, the counterion of which can be any of a variety of anions that does not contain an acidic proton. For example, the anion can be a sulfate, nitrate, nitrite, cyanide, or halide. Preferably, the anion is a halide. More preferably, the anion of the Mg(II) salt is Cl.

Generally, the reducing agent can be any reducing agent that is capable of reducing Mg(II) salts in an ethereal, polyethereal, or hydrocarbon solvent. Any reducing agent having a reduction potential of about −1.5 volts or more negative will satisfy this relation. It is preferred, however, if the reducing agent has a reduction potential of about −1.8 volts or more negative, and most preferred if the reducing agent has a reduction potential of about −2.0 volts or more negative. Preferably, the reduction takes place in an ethereal or polyethereal solvent, and more preferably in tetrahydrofuran (THF).

Examples of suitable reducing agents include alkali metal salts of aromatic anions, such salts being, for instance, sodium or lithium naphthalenide, anthracenide, or biphenylide. Preferably, the reducing agent is a combination of an alkali metal cation and an anion of an aromatic electron transfer compound, such as biphenyl, anthracene, or naphthalene. Most preferably, the reducing agent is preformed. Of the preformed alkali metal arene salts, the most preferred is lithium naphthalenide.

By "preformed" it is meant that the alkali metal and about 1-1.2 equivalents of the arene are allowed to react substantially completely, i.e., until substantially all the alkali metal is consumed, before contacting any magnesium salts. The formation of the preformed reducing agent typically takes place in an ethereal, polyethereal, or hydrocarbon solvent, and generally is substantially complete in about 2 hours.

The highly reactive magnesium species is generally in the form of a black metal powder. This powder typically settles out of solution after a few hours leaving a clear solution. The solvent can then be removed via cannula. The metal powder can then be washed to remove the electron carrier as well as the alkali metal salt produced from the cation of the aromatic reducing agent and the anion of the magnesium salt starting material if so desired. Although the highly reactive magnesium is preferably washed prior to further reaction, it can contain residual alkali metal salt. The highly reactive magnesium species is preferably utilized within a short period of time after its preparation.

The process for reduction to produce the highly reactive magnesium species of the present invention is conducted under conditions designed to prevent its reoxidation. Generally, these conditions include use of ethereal, polyethereal, or hydrocarbon solvents and the exclusion of oxygen. Preferably, these conditions include ambient temperatures, an inert atmosphere, e.g., an argon or nitrogen atmosphere, a reaction time of about 30 minutes, and an ether or polyether solvent such as diethyl ether, dimethyl ether, tetrahydrofuran, and the like, or a hydrocarbon solvent. Typically, the molar ratio of the reducing agent to the Mg(II) salt is about 2:1 for an equivalent amount; however, the Mg(II) salt can be in excess. Preferably, the Mg(II) salt is present in an amount of about 0.8-1.2 equivalents per equivalent of reducing agent.

Although the magnesium species can be maintained for a time under these conditions, it is also quite reactive. Consequently, it is preferably synthesized and used immediately or within a very short period of time. However, it can be stored for several days and much longer at lower temperatures under an inert atmosphere.

The magnesium species of this invention will react with symmetrical and unsymmetrical 1,3-diene compounds to produce selectively reactive (2-butene-1,4-diyl)magnesium compounds. These organomagnesium species undergo a variety of reactions to produce both novel organic compounds and novel synthetic methods for known organic compounds. One type of novel (2-butene-1,4-diyl)magnesium complex results from the reaction of this highly reactive magnesium with cyclic hydrocarbons containing at least two conjugated exocyclic double bonds, such as occur in 1,2-dimethylenecyclohexane, 1,2-dimethylenecyclopentane, and 1,2-dimethylenecycloheptane, for example.

Spiroannelation

Highly reactive magnesium reacts smoothly with cyclic hydrocarbons containing at least two conjugated exocyclic double bonds to produce the corresponding (2-butene-1,4-diyl)magnesium complexes in high yield. The cyclic hydrocarbons can be any of a variety of cyclic alkanes or cyclic alkenes containing at least two conjugated exocyclic double bonds providing, however, that any double bonds in the ring are not in conjugation with the exocyclic double bonds. Preferably, these cycloalkanes do not contain any additional functional groups that react with the highly reactive magnesium preferentially to the conjugated exocyclic double bond functionalities. More preferably, the cyclic hydrocarbons are cycloalkanes containing at least two exocyclic double bonds. Most preferably, the cycloalkanes are 1,2-dimethylenecycloalkanes, such as 1,2-dimethylenecyclohexane, 1,2-dimethylenecyclopentane, and 1,2-dimethylenecycloheptane. These resulting (2-butene-1,4-diyl)magnesium complexes prepared from cyclic hydrocarbons with conjugated exocyclic double bonds react with a variety of electrophiles, i.e., compounds that are deficient in electrons, to form spirocycles (Tables I and II). Spirocycles, particularly the spiro[4.5]decane and spiro[5.5]undecane ring systems, constitute the basic carbon framework found in a wide variety of naturally occurring sesquiterpenes. Herein, spirocycles refer to molecular structures with two rings having one atom in common.

The electrophiles include, but are not limited to, organodihalides, such as 1,2-dibromoethane, 1,3-dibromopropane, 1,4-dibromobutane, and 1,5-dibromopentane, organoditosylates, such as ethylene glycol di-p-tosylate, haloalkylnitriles, such as $[Br(CH_2)_n]$ compounds wherein n=1-3, esters, acids, amides, and the like. The reactions with the electrophiles typically yield spirocycles in isolated yields greater than about 40%, and often greater than about 50%.

Significantly, a wide variety of ring sizes can be generated using this approach, making this an advantageous method for the easy preparation of a wide variety of spirocycles. Furthermore, the spirocycles typically formed by this method contain functional groups, such as an exocyclic double bond or a keto group, in one of the rings that can be used for further elaboration of these molecules.

The reaction conditions for production of (2-butene-1,4-diyl)magnesium complexes resulting from the reaction of highly reactive magnesium with cyclic hydrocarbons having conjugated exocyclic double bonds include ambient temperatures, the absence of oxygen, and an excess of highly reactive magnesium. Generally, these conditions include use of ethereal, polyethereal, or hydrocarbon solvents. Preferably, the reactions are carried out under an inert atmosphere of argon or nitrogen with a ratio of magnesium to cyclic hydrocarbon present in a range of about 1:1 to 2:1 molar equivalents. The reaction time is preferably 3–4 hours, and the solvent is preferably an ether or polyether solvent such as diethyl ether, dimethyl ether, tetrahydrofuran, and the like. More preferably, the solvent is tetrahydrofuran.

The subsequent reactions of these (2-butene-1,4-diyl)magnesium complexes with electrophiles to produce spirocycles include temperatures of less than about 100° C., preferably between about −80° C. and about 80° C., and the absence of oxygen. Generally, these reactions are carried out in ethereal, polyethereal, or hydrocarbon solvents. Preferably, the reactions are carried out in tetrahydrofuran under an inert atmosphere of argon or nitrogen at a temperature of about −78° C. with subsequent warming. The keto-functionalized products also include a step whereby $H_3O^+$ is added subsequent to warming.

Fused Ring Carbocyclic Alcohols and $\beta,\gamma$-Unsaturated Ketones

This chemistry can also be extended to the construction of fused rings. Many naturally occurring sesquiterpenes contain such fused carbocyclic skeletons. For example, fused carbocyclic alcohols can be obtained by the reaction of (2-butene-1,4-diyl)magnesium complexes prepared from cyclic hydrocarbons containing two conjugated exocyclic double bonds with carboxylic esters and acids. These reactions can be also used to prepare $\beta,\gamma$-unsaturated ketones simply by controlling the reaction temperature (Table III).

This approach is of general synthetic utility for the preparation of fused carbocyclic alcohols or $\beta,\gamma$-unsaturated ketones depending on the reaction temperatures. That is, treatment of (2-butene-1,4-diyl)magnesium complexes, prepared as described above, with carboxylic esters or acids at temperatures below about −10° C. and quenching the reactions at −10° C. results in the formation of $\beta,\gamma$-unsaturated ketones in isolated yields of at least about 50%. On the other hand, warming the mixture to room temperature or greater, preferably up to refluxing temperatures, followed by workup and isolation affords a fused carbocyclic alcohol in isolated yields of at least about 50%. The further addition of acid chlorides at temperatures below about −20° C. alternatively can lead to the formation of spirocycles containing a three-membered ring.

The reactions leading to $\beta,\gamma$-unsaturated ketones are typically regioselective, i.e., there is generally no double bond scrambling. This feature should provide a new entry to the regioselective synthesis of $\beta,\gamma$-unsaturated ketones from 1,3-dienes. Furthermore, the overall process from 1,2-dimethylenecycloalkanes to the corresponding fused carbocyclic alcohols represents a formal [4+1] annulation which serves as an easy route to the hydroindene, hydropentalene, and hydroazulene bicyclic systems.

The carboxylic esters or acids used in these reactions can be any of a variety, such as, for example ethyl acetate, ethyl butyrate, ethyl benzoate, and acetyl chloride. These reactions can be carried out in ethereal, polyethereal, or hydrocarbon solvents. Preferably, they are carried out in the tetrahydrofuran.

Preparation of Silicon-Containing Spiroheterocycles

One of the useful applications of substituted (2-butene-1,4-diyl)magnesium complexes formed from unsymmetrical 1,3-dienes is the facile synthesis of silicon-containing spirocyclic compounds. Significantly, double annelation can be accomplished in one step by treating unsymmetrical (2-butene-1,4-diyl)magnesium complexes with a silicon halide, such as $SiCl_4$, for example, to form spiroheterocycles (Table IV).

Although it is particularly difficult to prepare unsymmetrical (2-butene-1,4-diyl)magnesium complexes from ordinary magnesium due to extensive polymerization, the use of highly reactive magnesium circumvents this problem. For example, an excess of newly generated highly reactive magnesium reacts with unsymmetrical 1,3-dienes, such as, for example, isoprene, myrcene, or 2-phenyl-1,3-butadiene, in an ethereal, polyethereal, or hydrocarbon solvent at room temperature in about 2 hours to give the corresponding unsymmetrical (2-butene-1,4-diyl)magnesium complexes. The reactions are preferably carried out in THF. The color of the resulting complexes varies with the diene: pale orange for isoprene; light olive for myrcene; and reddish brown for 2-phenyl-1,3-butadiene.

Typically, the reaction involves the combination of an excess of an unsymmetrical 1,3-diene with a silicon halide under extremely mild conditions. The reaction conditions include temperatures below about 25° C., and preferably between about −80° C. and about 0° C. Most preferably the reactions are carried out at −78° C. for about 30 minutes followed by warming to 0° C. The reactions are typically carried out in an ethereal, polyethereal, or hydrocarbon solvent and in the absence of oxygen. Preferably, the reactions are carried out under an inert atmosphere such as nitrogen or argon in tetrahydrofuran.

Regioselective Reactions of Unsymmetrical (2-Butene-1,4-diyl)magnesium Reagents with Two Different Electrophiles One of the major differences in chemistry between unsymmetrical and symmetrical (2-butene-1,4-diyl)magnesium complexes originates from the fact that the former possesses four totally different reactive sites and the latter has only two nonidentical nucleophilic centers. Accordingly, the regiochemistry of electrophilic attack is one of the essential problems associated with the reactions of unsymmetrical (2-butene-1,4-diyl)magnesium complexes. Treatment of unsymmetrical (2-butene-1,4-diyl)magnesium complexes with triorganosilyl chloride followed by cyclohexanone affords a stepwise addition across a terminal double bond with high regioselectivity. The results of the regioselective reactions are summarized in Table V.

Typically, the conditions of the regioselective reactions include temperatures below about 25° C., preferably within a range of about −80° C. and 0° C., and the absence of oxygen. The solvent is generally an ethereal, polyethereal, or hydrocarbon solvent. Preferably, the regioselective reactions are carried out with the unsymmetrical (2-butene-1,4-diyl)magnesium complex and an organosilicon reagent, such as Me$_3$SiCl, in THF at a temperature between about −80° C. and 0° C. This is followed by the addition of an excess of a second electrophile, such as cyclohexanone. Subsequently, the reaction mixture is warmed to room temperature and the products isolated.

In a typical example, it is believed that the initial attack of the complex by the organosilicon reagent determines the selectivity, which was found to be generally dependent on both the diene substrate and the initial electrophile. The reaction of (2-methyl-2-butene-1,4-diyl)magnesium with trimethylsilyl chloride resulted in initial attack at the 4 or 1-position, producing two isomers of allylic Grignards. Reports of $^1$H NMR studies reveal that substituted allylic Grignard reagents exist as a rapidly equilibrating mixture of Z and E primary stereoisomers. Treatment of the allylic Grignards with cyclohexanone leads to overall additions across a terminal double bond.

Increasing the size of the organosilicon reagent results in increased regioselectivity. This was demonstrated by using tri(n-butyl)silyl chloride as the initial electrophile. Larger substituents at the 2-position of the diene can also increase selectivity. For example, the magnesium complex of myrcene reacted with trimethylsilyl chloride, followed by cyclohexanone, to yield 1-(2-(4-methyl-3-pentenyl)-1-trimethylsilylmethyl-2-propenyl)cyclohexanol and 1-(1-ethenyl-5-methyl-1-trimethylsilylmethyl-4-hexenyl)cyclohexanol in a 94:6 ratio. Furthermore, a single isomer is obtained in excellent yield by replacing the first electrophile with tri(n-butyl)silyl chloride.

The invention will be further exemplified with respect to the various specific and preferred embodiments and techniques. It should be understood, however, that many variations and modifications may be made while remaining within the scope of the invention.

EXPERIMENTAL EXAMPLES

General Aspects $^1$H NMR (360 MHz) spectra were recorded in CDCl$_3$ solution unless specified. All chemical shifts are reported in parts per million ($\delta$) downfield from internal standard tetramethylsilane. Fully decoupled $^{13}$C NMR (50 MHz) spectra were recorded in CDCl$_3$ solution. The center peak of CDCl$_3$ (77.0 ppm) was used as the internal reference. FTIR spectra are reported in cm$^{-1}$. Mass spectra were performed by the Midwest Center for Mass Spectrometry at the University of Nebraska-Lincoln.

All manipulations were carried out under an atmosphere of argon on a dual manifold vacuum/argon system. The Linde TM prepurified grade argon was further purified by passage through a BASF TM R3-11 catalyst column at 150° C., a phosphorous pentoxide column, and a column of granular potassium hydroxide. Lithium, naphthalene, and MgCl$_2$ were weighed out and charged into reaction flasks under argon in a Vacuum Atmospheres Company dry box. Tetrahydrofuran was distilled from Na/K alloy under an atmosphere of argon immediately before use. All other reagents were used as received unless otherwise specified.

Gas chromatographic analyses were done on a Hewlett-Packard TM 5890A chromatograph using stainless steel columns (12 feet × ⅛ inches) packed with OV-17 (3%) on 100/120 Chromosorb TM G-AW or SE-30 (5%) on 100/120 Chromosorb TM G-NAW. Preparative gas chromatographic separations were obtained on a Varian Aerograph TM (model 920) chromatograph equipped with a stainless steel column (12 feet × ¼ inches) packed with GP 10% SP 2100 on 100–120 Supelcoport. Analytical thin-layer chromatography was performed using Merck TM 5735 indicating plates precoated with silica gel 60 F$_{254}$ (layer thickness 0.2 mm). Preparative thin-layer chromatographic separations were obtained using Anatech TM silica gel GF (layer thickness 2 mm) preparative plates or using Whatman TM PLKC 18F linear-K reversed phase preparative plates (layer thickness 1 mm). Liquid chromatographic purifications were performed by flash column chromatography using glass columns packed with Merck TM silica gel 60 (230–400 mesh). Low-temperature conditions were obtained utilizing a Neslab Endocal TM ULT-80 refrigerated circulating bath or utilizing dry ice/acetone baths.

Highly Reactive Magnesium

Highly reactive magnesium was prepared by the reduction of anhydrous magnesium chloride with lithium using naphthalene as an electron carrier. Highly reactive magnesium can also be prepared from the reduction of magnesium chloride by preformed lithium naphthalenide. In a typical preparation, lithium (10.0 mmol) and naphthalene (10.8 mmol) in freshly distilled THF (15 mL) were stirred under argon until the lithium was completely consumed (approximately 2 hours). The resulting dark green lithium naphthalenide was then transferred dropwise via a cannula into a THF solution (10 mL) of anhydrous magnesium chloride (4.8 mmol). The mixture was stirred at room temperature for 30 minutes. The newly formed magnesium slurry was allowed to settle for at least 3 hours and then the supernatant was drawn off via a cannula. Freshly distilled THF was added, followed by the appropriate 1,3-diene. [Note: The mmoles of highly reactive magnesium refer to the theoretical amount possible, based on the original amount of magnesium chloride.]

Spiroannelation

Initial attempts to prepare a (2-butene-1,4-diyl)magnesium complex by reacting 1,2-dimethylenecyclohexane with ordinary metallic magnesium were not successful. Highly reactive magnesium, prepared by the reduction of magnesium chloride with lithium using naphthalene as an electron carrier, reacted smoothly with 1,2-dimethylenecyclohexane in THF at ambient temperature, giving the corresponding (2-butene-1,4-diyl)magnesium complex in high yield.

In a typical preparation, 1,2-dimethylenecyclohexane (2.0 mmol) was added via a disposable syringe to the newly prepared highly reactive Mg (3.0 mmol) in THF (15 mL). The mixture was stirred for 3–4 hours at room temperature under argon. The yellowish gold THF solution of the complex was separated from the excess magnesium either by: filtration; or by transferring the solution via cannula to another flask after the mixture had settled and the solution had became transparent (approximately 2 hours). Bis-electrophiles were added to the freshly prepared THF solutions of the magnesium complexes of 1,2-dimethylenecycloalkanes at −78° C. The reaction mixture was then stirred at −78° C. for 1 hour prior to warm up. This same method can be extended to other 1,2-dimethylenecycloalkanes, such as 1,2-dimethylenecyclopentan and 1,2-dimethylenecycloheptane.

Significantly, treatment of this type of (2-butene-1,4-diyl)magnesium complex, i.e., those resulting from the reaction of highly reactive magnesium with cycloalkanes having two conjugated exocyclic double bonds, with biselectrophiles, especially 1,n-dibromoalkanes, gave spirocycles in good to excellent yields. The results are summarized in Table I. A major advantage of using (2-butene-1,4-diyl)magnesium complexes is that spiroannelation can be achieved in one synthetic operation.

TABLE I

Reactions of the Magnesium Complexes of 1,2-Dimethylenecycloalkanes with Bis-electrophiles

| Diene[a] | Electrophile | Conditions | Product[b] | % Yield[c] |
|---|---|---|---|---|
| 1 | Br(CH$_2$)$_5$Br | −78° C. to reflux | 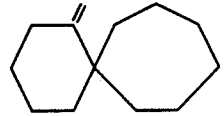 | 45 |
| 1 | Br(CH$_2$)$_4$Br | −78° C. to reflux | 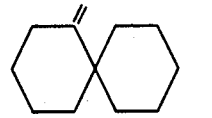 | 75 (81) |
| 1 | Br(CH$_2$)$_3$Br | −78° C. to room temp. | 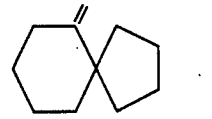 | 75 (87) |
| 1 | Br(CH$_2$)$_3$Br | −78° C. to −30° C. | 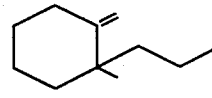 | 78[d] |
| 1 | Br(CH$_2$)$_2$Br | −78° C. to room temp. |  | — (15)[e] |
| 1 | TsO(CH$_2$)$_2$OTs | −78° C. to room temp. |  | 52 (67)[e] |
| 2 | Br(CH$_2$)$_3$Br | −78° C. to room temp. |  | 60 (70) |
| 3 | Br(CH$_2$)$_3$Br | −78° C. to room temp. |  | 77 (86) |

[a]1: 1,2-Dimethylenecyclohexane; 2: 1,2-Dimethylenecyclopentane; 3: 1,2-Dimethylenecycloheptane.
[b]All new compounds have been fully characterized by $^1$H NMR, $^{13}$C NMR, IR and mass spectra.
[c]Isolated overall yields were based on 1,2-dimethylenecycloalkanes. GC yields are shown in parentheses.
[d]Protonation of the intermediate at −30° C. resulted in monoalkylation, yielding the corresponding bromoolefin containing a quaternary center.
[e]Attempts to generate a four-membered ring by treating the (2-butene-1,4-diyl)magnesium complex generated from 1a with 1,2-dibromoethane gave only low yields of 5-methylenespiro[3.5]nonane. This spirocycle was prepared in good yield by the use ethylene glycol di-p-tosylate in place of 1,2-dibromoethane in THF at −78° C. followed by warming to room temperature.

Keto-Functionalized Spirocycles

The (2-butene-1,4-diyl)magnesium complexes prepared from the reaction of highly reactive magnesium with cycloalkanes having two conjugated exocyclic double bonds also react with bromoalkylnitriles to generate keto-functionalized spirocycles. These magnesium complexes of 1,2-dimethylenecycloalkanes were prepared as described above. The bromonitriles were added to the THF solution of these complexes at −78° C. The reaction mixture was then stirred at −78° C. for 30 minutes prior to warming to room temperature. This was followed by adding $H_3O^+$ to the solutions. Table II summaries the results of these studies.

TABLE II

Reactions of the Magnesium Complexes of 1,2-Dimethylenecycloalkanes with Bromoalkylnitriles

| Diene[a] | Bromonitrile | Product[b] | % Yield[c] |
|---|---|---|---|
| 1 | BrCH₂CN | 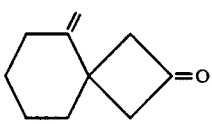 | 46 |
| 1 | Br(CH₂)₂CN | 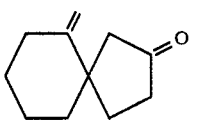 | 51 |
| 1 | Br(CH₂)₃CN | 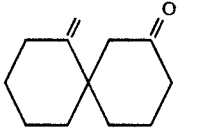 | 13 |
| 1 | Br(CH₂)₃CN | 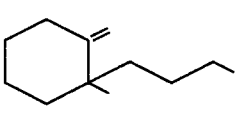 | 61[d] |
| 2 | Br(CH₂)₂CN | 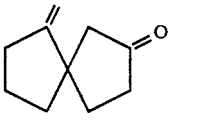 | 40 |
| 3 | Br(CH₂)₂CN | 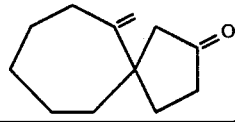 | 54 |

[a]1: 1,2-Dimethylenecyclohexane; 2: 1,2-Dimethylenecyclopentane; 3: 1,2-Dimethylenecycloheptane.
[b]All compounds have been completely characterized spectroscopically.
[c]Isolated overall yields were based on 1,2-dimethylenecycloalkanes.
[d]Protonation at −40° C. resulted in the survival of the cyano group, establishing where the initial attack occurred.

Fused Ring Carbocyclic Alcohols and β,γ-Unsaturated Ketones

Table III lists representative results for the reactions of magnesium complexes of 1,2-dimethylenecycloalkanes with carboxylic esters and acids. This approach is of general synthetic utility for the preparation of fused carbocyclic alcohols or β,γ-unsaturated ketones depending on the reaction temperatures. For example, treatment of the magnesium complex of 1,2-dimethylenecyclohexane with ethyl acetate at low temperatures (−78° to −10 ° C.) and quenching the reaction at −10 ° C. resulted in the formation of 2-methyl-1-cyclohexenyl-2-propanone in 72% isolated yield. On the other hand, warming the mixture to reflux followed by workup afforded a fused carbocyclic alcohol, in excellent yield.

The magnesium complexes of 1,2-dimethylenecycloalkanes were prepared as described above. The temperature of the reaction of each of these complexes with carboxylic esters and acids was typically maintained at or below −10° C. in order to obtain an enone product. In contrast, the reaction mixture was typically refluxed for complete formation of a fused carbocycle product. Satisfactory results were obtained in the reactions using ethyl acetate, ethyl butyrate, ethyl benzoate, and acetyl chloride.

TABLE III

Reactions of the Magnesium Complexes of 1,2-Dimethylenecycloalkanes with Esters and Acetyl Chloride

| Diene[a] | RC(O)X | Conditions[b] | Product[c] | % Yield[d] |
|---|---|---|---|---|
| 1 | CH₃COOEt | A | 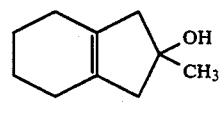 | 91 |
| 1 | CH₃COOEt | B | 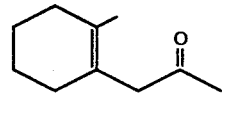 | 72 |
| 1 | CH₃COOEt then CH₃COCl | C | 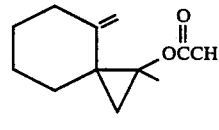 | 75 |

TABLE III-continued
Reactions of the Magnesium Complexes of 1,2-Dimethylenecycloalkanes with Esters and Acetyl Chloride

| Diene[a] | RC(O)X | Conditions[b] | Product[c] | % Yield[d] |
|---|---|---|---|---|
| 1 | CH$_3$CH$_2$COOEt | A |  | 96 |
| 1 | CH$_3$CH$_2$COOEt | B | 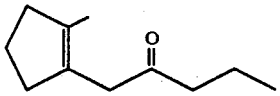 | 81 |
| 1 | PhCOOEt | A |  | 55 |
| 1 | PhCOOEt | B | 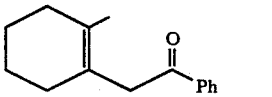 | 62 |
| 2 | CH$_3$CH$_2$COOEt | A | 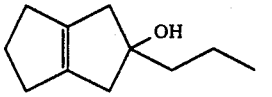 | 59 |
| 2 | CH$_3$CH$_2$COOEt | B | 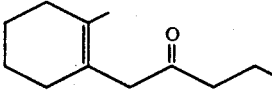 | 76 |
| 3 | CH$_3$CH$_2$COOEt | A |  | 74 |
| 3 | CH$_3$CH$_2$COOEt | B | 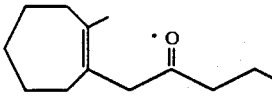 | 84 |
| 1 | CH$_3$COCl | A |  | 69 |
| 1 | CH$_3$COCl | D | 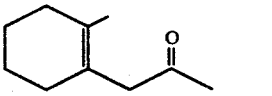 | 58 |
| 1 | 2CH$_3$COCl | E | 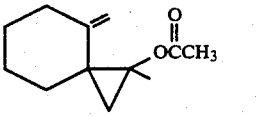 | 88 |

[a] 1: 1,2-Dimethylenecyclohexane; 2: 1,2-Dimethylenecyclopentane; 3: 1,2-Dimethylenecycloheptane.
[b] Conditions "A": stir at −78° C. for 30 minutes, allow solution to warm to room temperature, and then reflux for 30 minutes.
Conditions "B": stir at −78° C. for 30 minutes, allow solution to warm to −10° C., and then stir at −10° C. for 1 hour.
Conditions "C": stir at −78° C. for 30 minutes, allow solution to warm to −10° C., and then stir at −10° C. for 1 hour, add CH$_3$COCl at −20° C. and stir for 30 minutes, warm to room temperature.
Conditions "D": stir at −78° C. for 30 minutes, allow solution to warm to −20° C., and then stir at −20° C. for 30 minutes.
Conditions "E": stir at −78° C. for 30 minutes, allow solution to warm to room temperature.
[c] All new compounds have been fully characterized by $^1$H NMR, $^{13}$C NMR, IR and mass spectra.
[d] Isolated overall yields were based on 1,2-dimethylenecycloalkanes.

In a typical reaction, (2-methyl-2-butene-1,4-diyl)-magnesium in 20 mL of THF, which was freshly prepared from isoprene (0.250 g, 3.67 mmol) and excess highly reactive magnesium, was cooled to −78° C. SiCl4 (0.256 g, 1.50 mmol) was added via a disposable syringe. There was an instantaneous disappearance of a pale orange color. After being stirred at −78° C. for 1 hour, the mixture was gradually warmed to 0° C. and an aqueous solution of 1.5N HCl (15 mL) was added. The reaction mixture was washed with diethyl ether (20 mL). The aqueous layer was extracted with diethyl ether (2×20 mL). The organic portions were combined, washed with saturated aqueous NaHCO3 (2×20 mL) and brine (15 mL), and dried over anhydrous Na2SO4. Evaporation of solvents and flash column chromatography afforded 2,7-dimethyl-5-silaspiro[4,4]nona-2,7-diene. This compound has been previously reported to be difficult to prepare; however, utilization of magnesium complexes of 1,3-dienes allows the preparation to be carried out under extremely mild conditions.

1159, 997, 767, 742, 694 cm$^{-1}$; EIMS m/z (relative intensity) 288 (M+, 100), 158 (57), 105 (15), 71 (14); HRMS calcd for C20H20Si: 288.1334, found: 288.1328.

Unsymmetrical (2-butene-1,4-diyl)magnesium complexes were prepared as follows. Isoprene, myrcene, or 2-phenyl-1,3-butadiene was added to an excess of newly generated highly reactive magnesium in 20 mL of THF (typical equivalent ratio of Mg:diene=1.5:1 to 1.8:1). After being stirred at room temperature for 2 hours, the reaction mixture was allowed to stand until the solution became transparent (approximately 3 hours). Then the upper clear solution of magnesium complex was transferred via a cannula to another flask under argon. The appropriate electrophile was then added to this magnesium complex.

In a typical regioselective reaction of an unsymmetrical (2-butene-1,4-diyl)magnesium complex, a THF solu-

TABLE IV

Preparation of Silicon-Containing Spiroheterocycles from Substituted (2-butene-1,4-diyl)Magnesium

| Diene[a] | Electrophile[b] | Product(s)[c] | % Yield |
|---|---|---|---|
| 4 | SiCl4 | 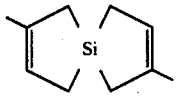 | 75 |
| 5 | SiCl4 | 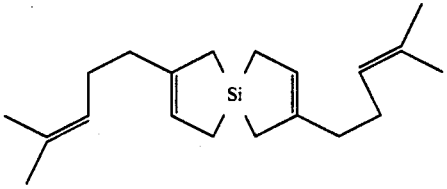 | 62 |
| 6 | SiCl4 | 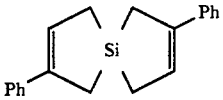 | 34 |

[a]4: isoprene; 5: myrcene; 6: 2-phenyl-1,3-butadiene.
[b]Electrophiles were added to the THF solution of substituted (2-butene-1,4-diyl)magnesium complexes at −78° C. The reaction mixture was stirred at −78° C. for 30 minutes then warmed to 0° C. prior to workup.
[c]All new compounds were completely characterized spectroscopically.

2,7-Dimethyl-5-silaspiro[4,4]nona-2,7-diene (0.185 g, 75% yield): $^1$H NMR δ 5.53 (m, 2 H), 1.77 (t, J=1.0 Hz, 6 H), 1.48 (d, J=1.1 Hz, 4 H), 1.40 (s, 4 H); $^{13}$C NMR δ 140.2, 124.9, 22.6, 21.8, 17.8; IR (neat) 3005, 2958, 2927, 2908, 2879, 2848, 1637, 1448, 1433, 1213, 1161, 1022, 756 cm$^{-1}$; EIMS m/z (relative intensity) 164 (M+, 73), 149 (3), 136 (8), 122 (12), 109 (4), 96 (100).

2,7-Di(4-methyl-3-pentenyl)-5-silaspiro[4,4]nona-2,7-diene (62% yield): $^1$H NMR δ 5.55 (s, 2 H), 5.09 (s, 2 H), 2.09 (s, 8 H), 1.67 (s, 6 H), 1.59 (s, 6 H), 1.47 (s, 4 H), 1.40 (s, 4 H); $^{13}$C NMR δ 144.2, 131.3, 124.5, 124.1, 36.8, 26.4, 25.7, 19.4, 17.7, 17.3; IR (neat) 3001, 2966, 2912, 2879, 1631, 1448, 1375, 1161, 823, 760; EIMS m/z (relative intensity) 300 (M+, 15), 257 (6), 231 (9), 203 (4), 175 (5), 163 (100), 135 (6), 121 (3), 109 (7), 95 (13), 69 (44); HRMS calcd for C20H32Si: 300.2273, found: 300.2278. Anal. calcd: C, 79.93; H, 10.73. Found: C, 80.24; H, 11.12.

2,7-Diphenyl-5-silaspiro[4,4]nona-2,7-diene (34% yield): $^1$H NMR δ 7.55-7.49 (m, 4), 7.36-7.20 (m, 6 H), 6.44 (s, 2 H), 1.96 (s, 4 H), 1.80 (s, 4 H); $^{13}$C NMR δ 141.9, 140.4, 128.2, 127.1, 126.8, 125.6, 18.3, 18.2; IR (neat) 3080, 3057, 3020, 2916, 2879, 1604, 1493, 1444, tion of the complex (20 mL) prepared from isoprene (0.281 g, 2.06 mmol, technical grade) and activated magnesium (3.44 mmol) was cooled to −78° C. Me3SiCl (0.171 g, 1.57 mmol) was added via a disposable syringe. The reaction mixture was stirred at −78° C. for 1 hour, and then it was gradually warmed to 0° C. Excess cyclohexanone (0.278 g, 2.83 mmol) was added at 0° C. The reaction mixture was warmed to room temperature and stirred for 1 hour. An aqueous solution of HCl (1.5N, 10 mL) was added at 0° C. The mixture was washed with diethyl ether (20 mL), and the aqueous layer was extracted with diethyl ether (2×20 mL). The combined organic phases were washed with a saturated aqueous solution of NaHCO3 (2×15 mL) and brine (20 mL) and dried over MgSO4. Removal of solvents and flash column chromatography (eluted by hexanes-/Et2O, 98:2) gave 1-(2-methyl-1-trimethylsilylmethyl-2-propenyl)cyclohexanol as the major isomer (0.372 g, 77%) and 1-(1-methyl-1-trimethylsilylmethyl-2-propenyl)cyclohexanol as the minor isomer (0.025 g, 5%) the major isomer was eluted out before the minor isomer in 82% total yield.

TABLE V
Regioselective Reactions of Unsymmetrical (2-butene-1,4-diyl)magnesium Complexes with Two Different Electrophiles

| Diene[a] | R₃SiCl[b] | Product(s)[c,d] | % Yield |
|---|---|---|---|
| 4 | (CH₃)₃SiCl | 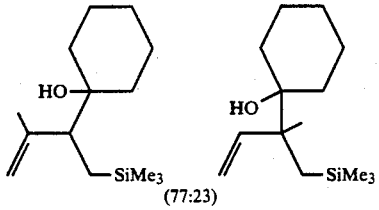 (77:23) | 91 |
| 4 | (n-Butyl)₃SiCl | 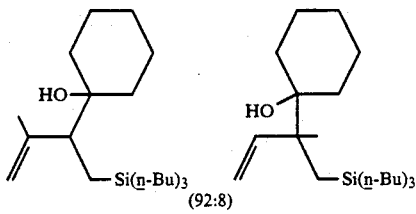 (92:8) | 94 |
| 5 | (CH₃)₃SiCl | 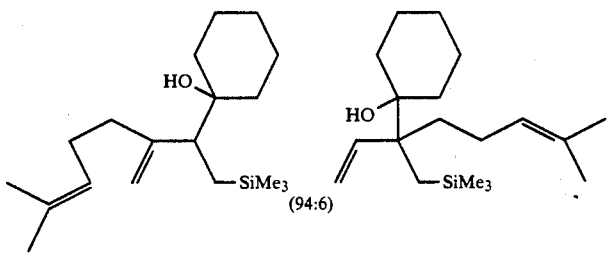 (94:6) | 82 |
| 5 | (n-Butyl)₃SiCl | 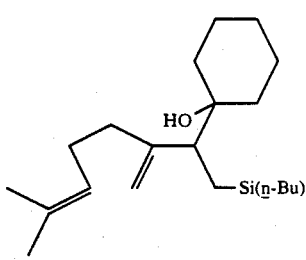 | 94 |
| 6 | (CH₃)₃SiCl | 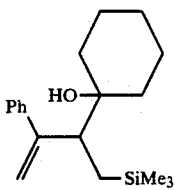 | 95 |
| 6 | (n-Butyl)₃SiCl | 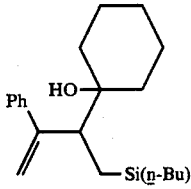 | 92 |

[a] 4: isoprene; 5: myrcene; 6: 2-phenyl-1,3-butadiene.
[b] R₃SiCl was added at −78° C. The rection mixture was stirred at −78° C. for 1 hour and then warmed to 0° C. prior to the addition of cyclohexanone.
[c] The compositions of all products (or major isomers) were determined by high resolution mass spectroscopy and/or elemental analyses. The structures of all compounds were established by ¹H NMR, ¹³C NMR, IR and mass spectra.
[d] Ratios of isomers were given in parentheses. Individual isomers were separated by chromatography.

1-(2-Methyl-1-trimethylsilylmethyl-2-propenyl)cyclohexanol and 1-(1-Methyl-1-trimethylsilylmethyl-2-propenyl)cyclohexanol (77:23, 91% total yield). Major isomer: $^1$H NMR δ 4.85 (m, 1 H), 4.76 (m, 1 H), 2.14 (dd, J =11.7, 3.4 Hz, 1 H), 1.74 (dd, J=1.2, 0.7 Hz, 3 H), 1.65-1.10 (m, 10 H), 0.82-0.68 (m, 2 H), −0.03 (s, 9 H); $^{13}$C NMR 147.0, 114.1, 73.0, 52.6, 35.6, 35.5, 25.8, 22.3, 22.1, 14.0, -1.1; IR (neat) 3487 (br), 3068, 2933, 2858, 1639, 1448, 1373, 1246, 964, 889, 862, 841 cm$^{-1}$; HRMS (FAB) calcd for [C$_{14}$H$_{28}$OSi+Li]+: 247.2070, found: 247.2075. Anal. Calcd for C$_{14}$H$_{28}$OSi: C, 69.93; H, 11.74. Found: C, 69.46; H, 11.97. Minor isomer: $^1$H NMR δ 5.91 (dd, J=17.6, 10.8 Hz, 1 H), 5.13 (dd, J=10.8, 1.6 Hz, 1 H), 5.01 (dd, J=17.6, 1.6 Hz, 1 H), 1.67-1.20 (m, 10 H), 1.08 (d, J=1.0 Hz, 3 H), 0.95 (dd, J=14.2, 1.0 Hz, 1 H), 0.80 (d, J=14.2 Hz, 1 H), −0.01 (s, 9 H); $^{13}$C NMR δ 145.6, 114.0, 75.3, 46.8, 31.3, 30.5, 25.8, 24.2, 22.2, 22.0, 19.4, 1.00; IR (neat) 3492 (br), 3080, 2935, 2860, 1631, 1448, 1415, 1375, 1248, 1223, 910, 864, 839 cm$^{-1}$; EIMS m/z (relative intensity) 225 ([M—CH$_3$]+, 0.7), 207 (0.6), 183 (0.3), 171 (5.3), 142 (12), 99 (27), 73 (100); HRMS calcd for C$_{14}$H$_{28}$OSi and [M—CH$_3$]: 240.1909, 225.1675, found: 240.1897 (EI Peak Match), 225.1678.

1-(2-Methyl-1-tri(n-butyl)silylmethyl-2-propenyl)cyclohexanol and 1-(1-Methyl-1-(tri-n-butyl)silylmethyl-2-propenyl)cyclohexanol (92:8, 94% total yield). Major isomer: $^1$H NMR δ 4.85 (m, 1 H), 4.77 (d, J=1.9 Hz, 1 H), 2.12 (dd, J=8.5, 6.1 Hz, 1 H), 1.76 (d, J=0.4 Hz, 3 H), 1.68-1.10 (m, 22 H), 0.87 (t, J=7.0 Hz, 9 H), 0.76-0.70 (m, 2 H), 0.52-4.44 (m, 6 H); $^{13}$C NMR δ 147.2, 114.1, 73.2, 52.3, 35.6, 35.5, 26.9, 26.2, 25.9, 22.3, 22.2, 13.8, 12.4, 9.8; IR (neat) 3491 (br), 3068, 2954, 2924, 2870, 2856, 1637, 1456, 1375, 1196, 1082, 964, 887 cm$^{-1}$; EIMS m/z (relative intensity) 309 ([M—C$_4$H$_9$]+, 0.5), 297 (4.3), 268 (7.8), 199 (100), 143 (67), 99 (19); HRMS calcd for C$_{23}$H$_{46}$OSi and C$_{22}$$^{13}$CH$_{46}$OSi: 366.3318, 367.3347, found (EI Peak Match): 366.3301, 367.3338. Anal. Calcd: C, 75.33; H, 12.64. Found: C, 75.60; H, 12.77. Minor Isomer (difficult to isolate): $^1$H NMR δ 5.92 (dd, J=17.6, 10.8 Hz, 1 H), 5.11 (dd, J=10.8, 1.2 Hz, 1 H), 5.01 (dd, J=17.6, 1.2 Hz, 1 H), 1.70-1.10 (m, 22 H), 1.07 (s, 3 H), 0.88 (t, J=7.0 Hz, 9 H), 0.95-0.75 (m, 2 H), 0.53-0.45 (m, 6 H). 1-(2-(4-Methyl-3-pentenyl)-1-trimethylsilylmethyl-2-propenyl)cyclohexanol and 1-(1-Ethenyl-5-methyl-1-trimethylsilylmethyl-4-hexenyl)cyclohexanol (94:6). Major isomer: $^1$H NMR δ 5.17-5.09 (m, 1 H), 4.89 (s, 1 H), 4.86 (s, 1 H), 2.20-2.00 (m, 5 H), 1.67 (s, 3 H), 1.60 (s, 3 H), 1.68-1.05 (m, 10 H), 0.84-0.69 (m, 2 H), 0.03 (s, 9 H); $^{13}$C NMR δ 151.1, 131.5, 124.4, 111.4, 73.2, 53.0, 35.6, 35.5, 25.9, 25.8, 25.7, 22.3, 22.1, 17.6, 14.9, −0.9; IR (neat) 3485 (br), 3080, 2931, 2858, 1633, 1448, 1375, 1246, 972, 891, 860, 837 cm$^{-1}$; EIMS m/z (relative intensity) 290 ([M—H$_2$O]+, 0.3), 275 (0.2), 210 (7), 171 (28), 141 (87), 99 (16), 73 (100); HRMS calcd for C$_{19}$H$_{36}$OSi and C$_{18}$$^{13}$CH$_{36}$OSi: 308.2535, 309.2563, found (HREI Peak Match): 308.2530, 309.2559. Anal. Calcd: C, 73.96; H, 11.76. Found: C, 74.15; H, 11.80. Minor isomer: $^1$H NMR δ 5.81 (dd, J=17.6, 11.0 Hz, 1 H), 5.15-4.95 (m, 3 H), 2.10-0.95 (m, 14 H), 1.65 (s, 3 H), 1.59 (s, 3 H), 0.91 (d, J=15.0 Hz, 1 H), 0.75 (d, J=15.0 Hz, 1 H), 0.04 (s, 9 H); $^{13}$C NMR δ 145.5, 131.0, 125.3, 114.1, 75.8, 50.6, 33.3, 31.6, 31.5, 25.7, 24.0, 22.0, 21.8, 19.8, 17.8, 1.6; IR (neat) 3566 (br), 3080, 2933, 2858, 1631, 1450, 1375, 1259, 1246, 1155, 958, 912, 860, 845 cm$^{-1}$.

1-(2-(4-Methyl-3-pentenyl)-1-tri(n-butyl)silylmethyl-2-propenyl)cyclohexanol (94% yield): $^1$H NMR δ 5.17-5.09 (m, 1 H), 4.89 (s, 1 H), 4.88 (s, 1 H), 2.20-2.03 (m, 5 H), 1.67 (s, 3 H), 1.60 (s, 3 H), 1.70-1.10 (m, 22 H), 0.86 (t, J=7.2 Hz, 9 H), 0.78-0.73 (m, 2 H), 0.50-0.43 (m, 6 H); $^{13}$C NMR δ 151.2, 131.5, 124.3, 111.0, 73.4, 52.6, 35.6, 35.3, 26.9, 26.1, 25.9, 25.8, 25.7, 22.3, 22.1, 17.6, 13.8, 12.5, 10.5; IR (neat) 3491 (br), 3080, 2954, 2922, 2870, 2856, 1633, 1456, 1375, 1194, 964, 887 cm$^{-1}$; EIMS m/z (relative intensity) 336 ([M—C$_6$H$_{10}$O]+, 2.3), 297 (1.9), 199 (100), 159 (39), 143 (53), 103 (18); HRMS calcd for C$_{28}$H$_{54}$OSi and C$_{27}$$^{13}$CH$_{54}$OSi: 434.3944, 435.3973, found (EI Peak Match): 434.3932, 435.3961. Anal. Calcd: C, 77.34; H, 12.53. Found: C, 77.22; H, 12.42.

1-(2-Phenyl-1-trimethylsilylmethyl-2-propenyl)cyclohexanol (95% yield): $^1$H NMR δ 7.43 (m, 2 H), 7.30 (m, 2 H), 7.23 (m, 1 H), 5.50 (s, 1 H), 5.16 (s, 1 H), 2.83 (t, J=6.9 Hz, 1 H), 1.69-1.00 (m, 10 H), 0.97 (d, J=6.9 Hz, 2 H), −0.03 (s, 9 H); $^{13}$C NMR δ 150.5, 144.5, 128.3, 127.1, 126.6, 115.5, 74.1, 48.7, 35.6, 35.0, 25.7, 22.0, 21.9, 16.9, −0.5; IR (neat) 3483 (br), 3082, 3057, 3030, 2935, 2860, 1618, 1599, 1574, 1495, 1448, 1248, 966, 903, 862, 843, 704 cm$^{-1}$; EIMS m/z (relative intensity) 284 ([M—H$_2$O]+, 0.3), 272 (0.3), 204 (30), 130 (8), 99 (13), 73 (100); HRMS (FAB) calcd for [C$_{19}$H$_{30}$OSi+Li]: 309.2226, found: 309.2221.

1-(2-Phenyl-1-tri(n-butyl)silylmethyl-2-propenyl)cyclohexanol (92% yield): $^1$H NMR δ 7.50-7.45 (m, 2 H), 7.35-7.28 (m, 2 H), 7.27-7.21 (m, 1 H), 5.53 (s, 1 H), 5.20 (s, 1 H), 2.83 (dd, J=11.3, 3.5 Hz, 1 H), 1.75-0.89 (m, 24 H), 0.85 (t, J=7.0 Hz, 9 H), 0.51-0.43 (m, 6 H); $^{13}$C NMR δ 150.4, 144.2, 128.3, 127.1, 126.6, 115.0, 74.4, 48.6, 35.6, 34.9, 26.8, 26.1, 25.8, 22.0, 13.7, 12.7; IR (neat) 3487 (br), 3082, 3055 3028, 2952, 2922, 2870, 2856, 1616, 1599, 1574, 1495, 1464, 1375, 1080, 964, 903, 706 cm$^{-1}$; EIMS m/z (relative intensity) 330 ([M—C$_6$H$_{10}$O]+, 2.2), 273 (1.2), 199 (38), 143 (68), 101 (18), 69 (100); HRMS calcd for C$_{28}$H$_{48}$OSi and C$_{27}$$^{13}$CH$_{48}$OSi: 428.3474, 429.3504, found (EI Peak Match): 428.3467, 429.3507.

The foregoing detailed description has been given for clarity of understanding only and no unnecessary limitations are to be understood therefrom. The invention is not limited to the exact details shown and described, for obvious modifications will occur to those skilled the art.

What is claimed is:

1. A method for the preparation of spirocycles comprising:
   a. contacting a magnesium(II) salt in an ethereal, polyethereal, or hydrocarbon solvent with a reducing agent having a reduction potential of about −1.5 volts, or more negative, to form a highly reactive magnesium species;
   b. contacting the highly reactive magnesium species with a cyclic hydrocarbon containir g at least two conjugated exocyclic double bonds to form a (2-butene-1,4-diyl)magnesium complex; and
   c. contacting the (2-butene-1,4-diyl)magnesium complex with an electrophile to form a spirocycle.

2. The method of claim 1 wherein the electrophiles are selected from the group consisting of organodihalides, organoditosylates, haloalkylnitriles, esters, and amides.

3. The method of claim 2 wherein the electrophiles are selected from the group consisting of alkyldibromides, alkylditosylates, and bromoalkylnitriles.

4. The method of claim 1 wherein the step of contacting the (2-butene-1,4-diyl)magnesium complex with an electrophile is carried out at a temperature below about 100° C.

5. The method of claim 2 wherein the step of contacting the (2-butene-1,4-diyl)magnesium complex with an electrophile is carried out in an ethereal or polyethereal solvent.

6. The method of claim 1 wherein the solvent used in the preparation of the highly reactive magnesium species is an ethereal or polyethereal solvent.

7. The method of claim 6 wherein the solvent is tetrahydrofuran.

8. The method of claim 1 wherein the reducing agent used in the preparation of the highly reactive magnesium species is an alkali metal salt of an aromatic anion.

9. The method of claim 8 wherein the reducing agent is selected from the group consisting of sodium or lithium naphthalenide, anthracenide, or biphenylide.

10. The method of claim 9 wherein the reducing agent is preformed lithium naphthalenide.

11. The method of claim 1 wherein the cyclic hydrocarbon is a cycloalkane containing two conjugated exocyclic double bonds.

12. The method of claim 11 wherein the cycloalkane is selected from the group consisting of 1,2-dimethylenecyclohexane, 1,2-dimethylenecyclopentane, and 1,2-dimethylenecycloheptane.

13. The method of claim 1 wherein the step of contacting the highly reactive magnesium species with a cyclic hydrocarbon is carried out in an ethereal or polyethereal solvent.

14. A method for the preparation of spirocycles comprising:
   a. contacting a magnesium(II) salt in an ethereal, polyethereal, or hydrocarbon solvent with an alkali metal salt of an aromatic anion to form a highly reactive magnesium species;
   b. contacting the highly reactive magnesium species with a cyclic hydrocarbon containing at least two conjugated exocyclic double bonds to form a (2-butene-1,4-diyl)magnesium complex; and
   c. contacting the (2-butene-1,4-diyl)magnesium complex with an electrophile at a temperature below about 100° C. to form a spirocycle.

15. The method of claim 14 wherein the alkali metal salt of an aromatic anion is selected from the group consisting of sodium naphthalenide, sodium anthracenide, sodium biphenylide, lithium naphthalenide, lithium anthracenide, and lithium biphenylide.

16. The method of claim 15 wherein the alkali metal salt of an aromatic anion is lithium naphthalenide.

17. A method for the preparation of spirocycles comprising:
   a. contacting a magnesium(II) salt in an ethereal, polyethereal, or hydrocarbon solvent with a reducing agent having a reduction potential of about −1.5 volts, or more negative, to form a highly reactive magnesium species, wherein the reducing agent is an alkali metal salt of an aromatic anion;
   b. contacting the highly reactive magnesium species with a cycloalkane containing at least two conjugated exocyclic double bonds to form a (2-butene-1,4-diyl)magnesium complex; and
   c. contacting the (2-butene-1,4-diyl)magnesium complex with an electrophile selected from the group consisting of organodihalides, organoditosylates, haloalkylnitriles, esters, and amides to form a spirocycle.

18. The method of claim 17 wherein the reducing agent is selected from the group consisting of sodium naphthalenide, sodium anthracenide, sodium biphenylide, lithium naphthalenide, lithium anthracenide, and lithium biphenylide.

19. The method of claim 17 wherein the Mg(II) salt is a Mg(II) salt of sulfate, nitrate, nitrite, cyanide, or halide.

20. The method of claim 19 wherein the Mg(II) salt is $MgCl_2$.

* * * * *

UNITED STATES PATENT AND TRADEMARK OFFICE
CERTIFICATE OF CORRECTION

PATENT NO. : 5,231,205

DATED : July 27, 1993

INVENTOR(S) : Rieke

It is certified that error appears in the above-identified patent and that said Letters Patent is hereby corrected as shown below:

Column 4, line 66, "[Br(CH$_2$)$_n$]" should read --[Br(CH$_2$)$_n$CN]--.

Column 9, line 9, "1,2-dimethylenencyclopentan" should read --1,2-dimethylenecyclopentane--.

Column 10, line 3, "biselectrophiles" should read --bis-electrophiles--.

Column 15, line 46, "δ4,4]" should read --[4,4]--.

Column 15, line 52, "(M$^+$, 73)," should read --(M$^{\cdot+}$, 73),--.

Column 15, line 59, "(M$^+$, 15)," should read --(M$^{\cdot+}$, 15),--.

Column 16, line 2, "(M$^+$, 100)," should read --(M$^{\cdot+}$, 100),--.

Column 17, line 2, "rection" should read --reaction--.

Column 19, line 41, "1-(2-(4-Methyl-3-pentenyl)-1-trimethylsilylmethyl-2-propenyl)cyclohexanol" should start a new paragraph.

UNITED STATES PATENT AND TRADEMARK OFFICE
CERTIFICATE OF CORRECTION

PATENT NO. : 5,231,205

DATED : July 27, 1993

INVENTOR(S) : Rieke

It is certified that error appears in the above-identified patent and that said Letters Patent is hereby corrected as shown below:

Column 19, line 52, "$([M-H_2O]^+,$" should read --$([M-H_2O]^{\cdot +},$--.

Column 20, line 6, "$([M-C_6H_{10}O]^+,$" should read --$([M-C_6H_{10}O]^{\cdot +},$--.

Column 20, line 21, "$([M-H_2O]^+,$" should read --$([M-H_2O]^{\cdot +},$--.

Column 20, lines 34-35, "$([M-C_6H_{10}O]^+,$" should read --$([M-C_6H_{10}O]^{\cdot +},$--.

Signed and Sealed this

Thirty-first Day of May, 1994

BRUCE LEHMAN

*Attest:*

*Attesting Officer*   *Commissioner of Patents and Trademarks*